US00PP34696P3

(12) United States Plant Patent
Olesen

(10) Patent No.: US PP34,696 P3
(45) Date of Patent: Nov. 1, 2022

(54) ROSE PLANT NAMED 'POULPAR130'

(50) Latin Name: *Rosa hybrida*
Varietal Denomination: Poulpar130

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/300,618

(22) Filed: Sep. 7, 2021

(65) Prior Publication Data

US 2022/0104412 P1 Mar. 31, 2022

(30) Foreign Application Priority Data

Sep. 21, 2020 (QZ) ..... PBR 2020/2272

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./116, 122
See application file for complete search history.

*Primary Examiner* — Annette H Para

(57) ABSTRACT

A new garden rose plant of the Miniature class which has abundant, red-purple flowers and attractive foliage. This new and distinct variety has shown to be uniform and stable in the resulting generations from asexual propagation.

1 Drawing Sheet

Botanical designation: *Rosa hybrida.*
Variety denomination: 'Poulpar130'.

This application claims priority to Plant Breeder's Rights Application Number 2020/2272, which was filed at the Community Plant Variety Rights Office in the European Union on Sep. 21, 2020, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2015 and the resulting seeds were planted in a controlled environment in Fredensborg, Denmark. The new variety, named 'Poulpar130', originated as a single seedling from the stated cross.

The new variety may be distinguished from its male pollen parent and female seed parent primarily by the following characteristics. The male pollen parent plant has mauve flowers while the new variety has red-purple flowers. The female seed parent plant has a growth height of 45 cm while the new variety grows to 30 to 35 cm in one season.

The objective of the hybridization of this rose variety was to create a new and distinct variety with unique qualities, such as:

1. Uniform and abundant red-purple flowers;
2. Vigorous, but compact growth when propagated on its own roots;
3. Exceptional disease resistance.

This combination of qualities is not present in previously available commercial cultivars of this type, known to the inventor, and distinguish 'Poulpar130' from all other varieties of which we are aware.

As part of the rose development program, Mogens N. Olesen germinated the seeds from the aforementioned hybridization during winter of 2015 and conducted evaluations on the resulting seedlings in a controlled environment in Fredensborg, Denmark. 'Poulpar130' was selected in the spring of 2016 by the inventor as a single plant from the progeny of the aforementioned hybridization.

Asexual reproduction of 'Poulpar130' by rooted cuttings was first done by Mogens N. Olesen in the nursery in Fredensborg, Denmark in July, 2016. This initial and other subsequent asexual propagations conducted in controlled environments have demonstrated that the characteristics of 'Poulpar130' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar130'. Specifically illustrated in the drawing are flowers in bud form and various stages of opening, fully open flowers viewed from above and the side, petals detached revealing reproductive flower parts, detached sepals showing pedicel and flower receptacle, bare stems, and leaves. Plants shown are 4 months of age.

DETAILED DESCRIPTION OF THE VARIETY

The following is a description of 'Poulpar130', as observed in its growth in a heated glass house in Odense Denmark. Observed plants are 4 months of age, and were grown on their own roots in 24 cm pots. Color references are made using The Royal Horticultural Society (London, England) Colour Chart, 2001, except where common terms of color are used.

For a comparison, several physical characteristics of the rose variety 'Poulpar072', U.S. Plant Pat. No. 24,931 dated Sep. 30, 2014 are compared to 'Poulpar130' in Chart 1.

CHART 1

| | 'Poulpar130' | 'Poulpar072' |
|---|---|---|
| Petal Count | 45 | 30 |
| Flower Diameter | 55 mm | 45 to 55 mm |
| General Tonality of Flower Color | Red-Purple Group 60D | Red Group 53B blended with intonations of Red-Purple Group N57B |

Flower and flower bud:

*Blooming habit.*—Continuous.

*Flower bud.*—Size: Upon opening, 20 mm in length from base of receptacle to end of bud. Bud diameter is 13 mm. Bud form: Ovoid. Bud color: As sepals divide petals are Red-Purple Group 61A. Sepal inner surface: Color: Yellow-Green Group 144B. Surface: Lightly pubescent. Sepal outer surface: Color: Yellow-Green Group 146B. Texture: Smooth. Sepal Shape: Apex: Cirrhose. Base: Flat at union with receptacle. Sepal Margin: Margins have weak foliaceous appendages on three of the five sepals. Sepal size: About 28 mm long, 6 mm wide. Receptacle: Texture: Smooth. Size: 5 mm in height, 7 mm wide. Color: Yellow-Green Group 144A. Shape: Funnel. Pedicel: Surface: Smooth. Length: 42 mm. Diameter: 3 mm on average. Color: Yellow-Green Group 144A. Strength: Strong.

*Flower bud development.*—Flower buds are borne singly.

*Flower bloom.*—Fragrance: Strong perfume. Duration: The blooms have a duration on the plant of approximately 19 days. Petals fall cleanly away from plant after flowers have fully matured. Size: Flower diameter is 55 mm when open. Flower depth is 21 mm. Flower shape: High centered, double, with a high pointed center which is tightly closed. Shape of flower, side view: The upper portion is flat and partially convex. The lower portion is flat.

*Petalage.*—Under normal conditions, flowers have about 45 petals.

*General tonality of flower.*—Open flowers are Red-Purple Group 60D.

*Petal color.*—Outer petals: Upper surface Red-Purple Group 61B. Splashed with Red-Purple Group 62C. Basal zone Yellow Group 2D. Lower surface Red-Purple Group 63A at marginal zone. Splashed with Red-Purple Group 65B. Basal zone Yellow Group 2D. Inner petals: Upper surface Red Group 53B splashed with intonations of Red-Purple Group 59A. Basal zone Yellow Group 7B. Lower surface Red-Purple Group 61B splashed with White Group N155B. Yellow 7B at basal zone.

*Petals.*—Petal Reflex: Somewhat reflexed. Margin: Entire and uniform. Moderate undulations. Shape: Broad and elliptic. Apex shape: Rounded. Base shape: Acute. Size: 30 mm (l)×31 mm (w). Texture: Smooth. Thickness: Average.

*Petaloids.*—Size: 11 mm (l) by 8 mm (w). Quantity: About 9. Shape: Elliptical with an acute base and rounded apices. Color: The upper surface is Red Group 53B with Yellow 7B at the point of attachment. The lower surface is Red-Purple Group 61B splashed with White Group N155B. Yellow 7C at the basal zone.

*Reproductive flower parts.*—Pollen: None observed. Anthers: Size: 2 mm in length. Color: Yellow Group 11B. Quantity: 35 on average. Filaments: Color: Yellow Group 11C. Length: 10 mm. Pistils: Length: 11 mm. Quantity: 23 on average. Stigmas: Color: Greyed Yellow 160D. Styles: Color: Greyed Yellow 160D. Location of stigmas: Superior in location relative to the length of the filaments and the height of the anthers. Hips: None Observed.

Plant:

*Plant growth.*—Upright. Plants are 30 to 35 cm in height, and 25 cm wide.

*Stems.*—Color of juvenile growth: Yellow-Green Group 144B. Color of mature growth: Yellow-Green Group 144A. Length: Canes are about 10 cm from the base of the plant to the flowering portion. Diameter: About 5 mm. Internodes: On mature canes about 39 mm between nodes. Surface Texture: Young wood: Smooth. Older wood: Smooth.

*Long prickles.*—Incidence: 4 prickles per 10 cm of stem. Size: Average length of prickles on mature stems is 6 mm. Shape: Upper portion is linear. Lower portion is concave. Color: Juvenile prickles: Greyed-Yellow Group 160D. Mature prickles: Greyed-Yellow Group 160D.

*Plant foliage.*—Compound leaf: About 90 to 60 mm (l)×110 (w). Quantity: 2 or 3 leaves per 10 cm of stem on average. Leaf bearing angle to the stem: 45 degrees. Color of juvenile foliage: Upper side: Yellow-Green Group 144A. Lower side: Yellow-Green Group 144B. Color of mature foliage: Upper side: Yellow-Green Group 147A. Lower side: Yellow-Green Group 146B.

*Plant leaves and leaflets.*—Stipules: Size: 4 mm long, 3 mm wide. Quantity: 2 per compound leaf. Shape: Linear, slightly broad based with outward extending apices. Margins: Finely serrated. Color: Yellow-Green Group 144A. Petiole: Length: 21 mm. Diameter: 1.5 mm. Upper surface color: Yellow-Green Group 144A. Lower surface color: Yellow-Green Group 144A. Rachis: Length: About 40 mm. Upper surface color: Yellow-Green Group 144A. Lower surface color: Yellow-Green Group 144A. Leaflet: Quantity: Normally 5 occasionally 7 leaflets. Margins: Serrated. Size: Terminal leaflets are about 30 mm long, 25 mm wide. Shape: Generally elliptical. Base: Rounded. Apex: Acute. Texture: Smooth. Thickness: Average. Arrangement: Odd pinnate. Venation: Reticulate. Glossiness: Not glossy.

*Disease resistance.*—Above average resistance to powdery mildew *Sphaerotheca pannosa* var. *rosae,* downy mildew *Peronospora sparsa,* rust *Phragmidium* spp., black spot *Diplocarpon rosae*, and *Botrytis cinerea* under normal growing conditions.

*Cold hardiness.*—The variety is tolerant to USDA Cold Hardiness Zone 6.

*Heat tolerance.*—The variety has been found to be suitable for climate conditions found in the American Horticulture Society heat zone 7.

I claim:

1. A new and distinct variety of rose plant of the Miniature rose class named 'Poulpar130', substantially as illustrated and described herein, due to its abundant red-purple flowers, disease resistance, and extended period of bloom.

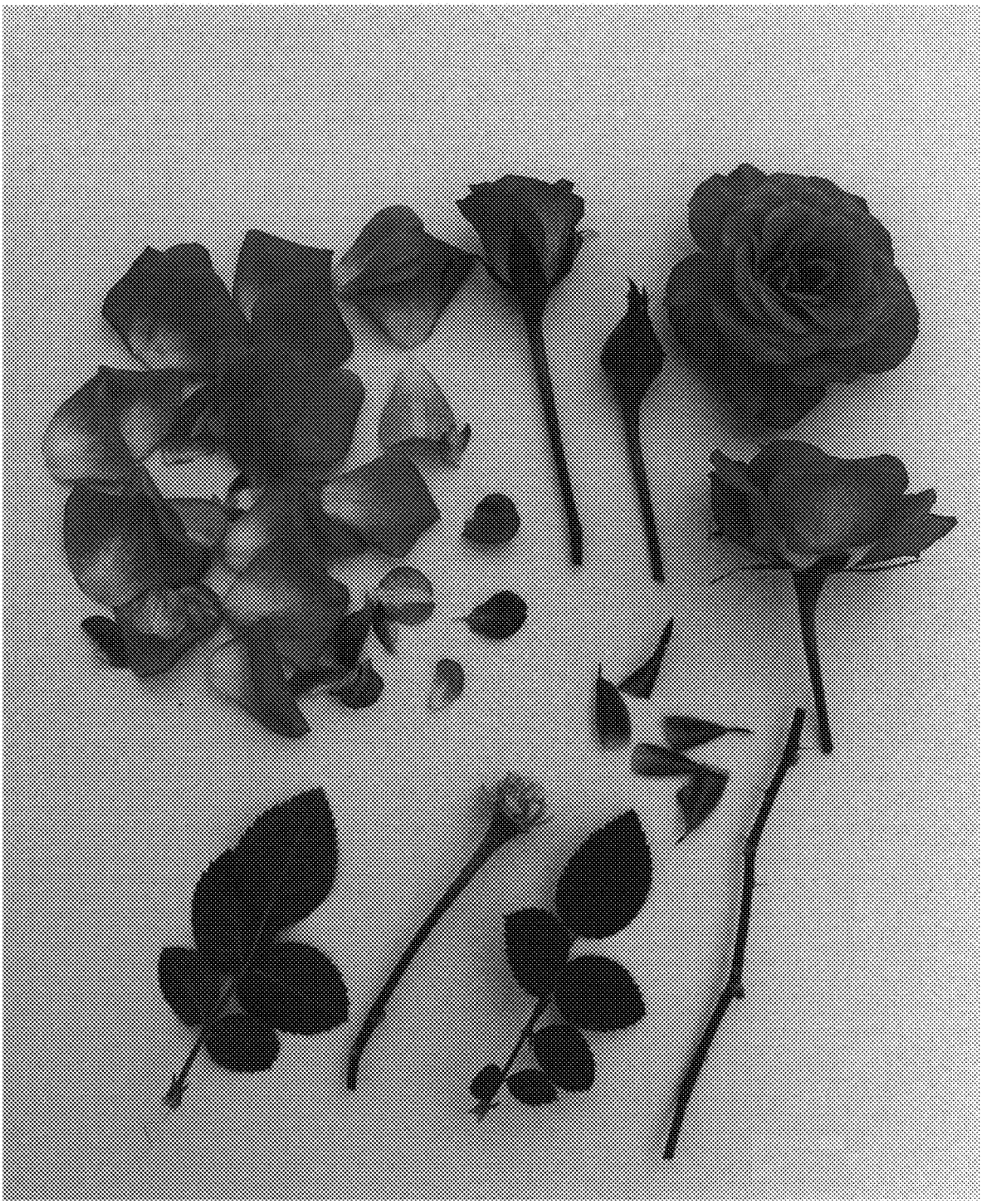

* * * * *